United States Patent [19]

Brown et al.

[11] Patent Number: 4,727,031

[45] Date of Patent: Feb. 23, 1988

[54] NUTRIENT FOR STIMULATING AEROBIC BACTERIA

[75] Inventors: Richard A. Brown, Trenton; Robert D. Norris, Cranbury, both of N.J.

[73] Assignee: International Technology Corporation, Torrence, Calif.

[21] Appl. No.: 669,288

[22] Filed: Nov. 8, 1984

[51] Int. Cl.$^4$ .................. C12N 1/38; C12N 1/20
[52] U.S. Cl. .................. 435/244; 435/253; 435/264
[58] Field of Search .............. 435/353, 802, 824, 830, 435/872, 243, 244, 264, 267, 818

[56] References Cited

U.S. PATENT DOCUMENTS

| | | | |
|---|---|---|---|
| 3,010,876 | 11/1961 | Badia et al. | 195/51 |
| 3,960,664 | 6/1976 | Olsen et al. | 195/59 |
| 4,402,986 | 9/1983 | Sinkoff et al. | 426/41 |

FOREIGN PATENT DOCUMENTS

WO8302952 9/1983 PCT Int'l Appl.

OTHER PUBLICATIONS

Dillon, A. P., *Pesticide Disposal and Detoxification Processes and Techniques,* New Jersey, Noyes Data Corporation, 1981, pp. 65–67.
Moat, A. G., *Microbial Physiology,* N.Y., John Wiley and Sons, Inc., 1979, p. 467.
Pollution Engineering, Dec. 1985, pp. 22–23.
*The New Encyclopaedia Brittanica,* 15th Edition, Macropaedia, vol. 11, Benton, 1974, (Chicago), p. 1023.
Busch, A. W., *Aerobic Biological Treatment of Waste Waters, Principles and Practice,* Oligodynamics Press, Houston (1971), pp. 29 to 33A and 107 to 116.

*Primary Examiner*—Margaret Moskowitz
*Attorney, Agent, or Firm*—Luedeka & Neely

[57] ABSTRACT

The present invention provides a composition of nutrients and a method using such a composition to stimulate the growth of aerobic bacteria, and particularly bacteria capable of biooxidizing contaminants in a subterranean formation.

16 Claims, 1 Drawing Figure

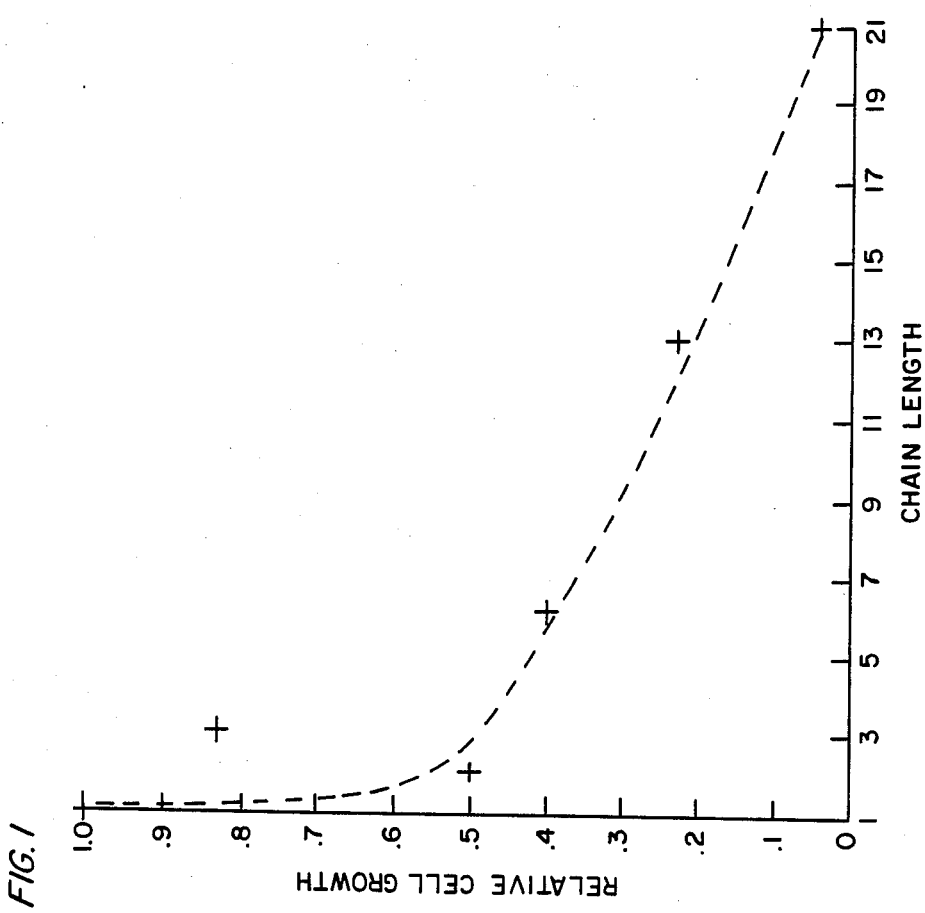

NUTRIENT FOR STIMULATING AEROBIC BACTERIA

The present invention is a nutrient composition suitable for stimulating the growth of aerobic bacteria and the method for using the composition to stimulate the growth of aerobic bacteria.

Nitrogen and phosphorus are known to be two of the essential elements for the growth of all living material, including bacteria. It is frequently necessary to supply both nitrogen and phosphorus and occasionally other nutrients and micronutrients to stimulate the growth of bacteria. Until recently all of the supplemental phosphorus supplied as a nutrient to stimulate the growth of bacteria was supplied as the orthophosphate because the orthophosphate anion is known to be smaller than an anion of a condensed phosphate and will thus diffuse more rapidly into the bacteria.

International Patent Publication No. WO 83/02952 teaches that the inorganic pyrophosphate ion can stimulate the growth of some anaerobic bacteria by supplying the energy of biological oxidation through the steps of:

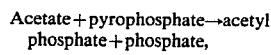
 1.

and

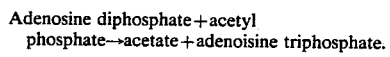
 2.

Thus, the pyrophosphate ion oxidizes adenosine diphosphate (ADP) to adenosine tripolyphosphate (ATP) in an anaerobic bacteria.

It is well known that ATP is the primary carrier of chemical energy in biological processes, losing in the process either one or two phosphate groups to form ADP and an orthophosphate ion, or adenosine monophosphate and a pyrophosphate ion. No advantage has been taught by other prior art to supply phosphorus to aerobic bacteria as a condensed phosphate such as a pyrophosphate or a tripolyphosphate.

According to Busch, *Aerobic Biological Treatment of Waste Waters*, Oligodynamics Press, Houston (1971) at page 107, which is incorporated herein by referenced, only nitrogen and phosphorus are critical, growth-limiting nutrients necessary to be added regularly to aerobically oxidize wastes and are generally added in the ratio of 5 parts of nitrogen per part of phosphorus. It is, therefore, an object of this invention to provide an improved nitrogen-phosphorus nutrient supplement for stimulating the growth of aerobic bacteria and an improved method for its use in such application.

In accordance with the present invention it has been found that an improved nutrient composition can be supplied to aerobic bacteria in which the nitrogen and the phosphorus are present in the ratio of not less that 0.8 parts by weight of total nitrogen per part by weight of total phosphorus and incorporating sufficient phosphorus as a short-chain condensed phosphate compound selected from the groups consisting of a pyrophosphate compound and a tripolyphosphate compound, whereby from 5% to 65% by weight of the combined orthophosphate and the condensed phosphate moiety in the composition is present as the condensed phosphate.

As taught by Busch supra, when the ratio of nitrogen to phosphorus of 5:1 is available to bacteria neither nutrient alone is the growth-limiting nutrient. It has been found that a ratio of total nitrogen to total phosphorus as low as 0.8:1 is suitable to stimulate the growth of bacteria even though nitrogen is then a limiting nutrient. Ratios of 10:1 or higher have been used in the prior art, and are also suitable for stimulating the growth of bacteria according to the present invention but do not offer any advantage over ratios ranging from 0.8:1 to 5:1.

For the maximum stimulation it is critical for the composition to contain the condensed phosphate as a tripolyphosphate compound.

It is also critical for maximum stimulation of aerobic bacteria for the short-chain condensed phosphates to be present in the range of from 25% to 45% by weight of the combined orthophoshate and condensed phosphate.

The nutrient composition may contain other conventional nutrients and micronutrients known by one skilled in the art to be essential to the aerobic bacteria.

It is completely unexpected to find that the tripolyphosphate ion can be utilized by bacteria. It is well-known that sodium tripolyphosphate (STPP) is used in large quantities as a detergent builder. However, the tripolyphosphate ion from this source is rarely, if ever, found in the environment. This is because the enzyme phosphatase, which is always present in sewage systems and septic tanks, rapidly hydrolyzes the tripolyphosphate ion to the orthophosphate ion. Because the tripolyphosphate ion is rapidly hydrolyzed it is unexpected that the aerobic bacteria could be adapted to utilize the tripolyphosphate ion. In addition it would normally be expected that the large size of the pyrophosphate and tripolyphosphate ions would decrease the rate of diffusion of phosphorus through the membranes of the bacteria and thus result in a decrease in the rate of growth of the bacteria. Thus it would be expected that the rate of stimulation of bacteria growth would decrease with an increase of chain length of a condensed phosphate.

It was found that the rate of growth of aerobic bacteria in general decreases as a function of phosphate chain length. The relative growth rate of bacteria utilizing a pyrophosphate (chain length of 2) as a phosphorus source is 50% the growth rate of bacteria utilizing orthophosphate (chain length of 1). On the other hand, the growth rate of bacteria utilizing a tripolyphosphate (chain length of 3) is 85% of the growth rate of bacteria utilizing an orthophosphate.

It was unexpectedly found that bacteria utilizing a combination of either tripolyphosphate or pyrophosphate ions and orthophosphate as a source of phosphorus had a growth rate greater than bacteria using an orthophosphate ion alone. There is no explanation presently available for this synergistic effect provided by a pyrophosphate or a tripolyphosphate ion in combination with an orthophosphate ion on the growth rate of aerobic bacteria.

The scope of the present invention is not limited to the preparation of a nutrient medium for the growth of aerobic bacteria, but also the preparation of a concentrated nutrient additive to supplement the nutrients already in a bacteria growth medium and to the process of growing bacteria in a media containing either a pyrophosphate or a tripolyphosphate ion and the orthophosphate ion in the relative proportion from 5% to 65% phosphorus as the condensed pyrophosphate or the tripolyphosphate ion and from 95% to 35% phosphorus as the orthophosphate ion. Preferably the tripolyphosphate is in the range of 25% to 45% of the phosphorus.

The maintenance of aerobic conditions is critical for the stimulation of aerobic oxidation by bacteria. Diffusion of dissolved oxygen into a large biomass is difficult according to Busch, *Aerobic Biological Treatment of Waste Waters*, at page 31. Therefore, it is preferable to supply oxygen to the bacteria by incorporating from 0.1 mg/l to 1000 mg/l hydrogen peroxide into the growth media.

The present invention is particularly adaptable to the stimulation of aerobic bacteria in commercial fermentation systems and in the environment where the tripolyphosphate ion is not naturally present. It is within the scope of the present invention to add a short-chain condensed phosphate such as a pyrophosphate or a tripolyphosphate either alone, or with sufficient orthophosphate to adjust the ratio of the short-chain condensed phosphate to the orthophosphate to within the range claimed in the present invention.

The present invention is particularly adapted for the stimulation of bacteria to oxidize contaminants, particularly in a subterranean formation. As both a pyrophosphate and a tripolyphosphate ion have the ability to sequester many metals, and an orthophosphate ion has the ability to precipitate many metals, it may be desirable to introduce the short-chain condensed phosphate ion and the orthophosphate ion in the medium separately and thereby modify the composition of the medium.

The short-chain condensed phosphate and the orthophosphate may be introduced into the solution in any conventional form, such as a solid salt, an acid, or as a solution. It is usually convenient to introduce the ions in the form of an acid salt of a metal ion or as an ammonium salt. One skilled in the art will readily recognize that it is desirable to introduce the nutrients not only in the most convenient but also most economical form.

The following examples are provided to illustrate the best mode of practicing the present invention to one skilled in the art and not to limit the scope of the invention.

In the following example water obtained from a gasoline spill site was cultured by the initial addition of approximately 0.01 g/l phosphate, 0.01 g/l ammonium chloride (a N:P ratio of 0.8) and 0.5 g/l gasoline. Approximately 1500 ml were filtered through glass wool, and 50 ml of the filtrate added to 32 oz. narrow mouth glass bottles. Nutrient concentrates were then added, followed by one drop of gasoline to each bottle. The bottles were capped using aluminum foil liners. One drop of gasoline was added every other day throughout the test period. At the end of the test period, 1 ml of 35% HCl was added to dissolve any precipitated metals. The samples were centrifuged, filtered, dried, and the solid mass weighed. The cell mass was used as the determinant of bacterial growth.

EXAMPLE 1

Nutrient cultures were prepared using mixtures of a pyrophosphate and an orthophosphate using the above procedure. Table I shows that pyrophosphate, when used with orthophosphates, stimulates the growth of indigeneous hydrocarbon utilizing bacteria. With these bacteria use of about 1%-75% of the total phosphorus as pyrophosphate resulted in an increased ratio of growth. However, pyrophosphate when used as the sole source of phosphorus or when supplying more than 90% of the phosphorus, is less effective than orthophosphate. These results demonstrate (1) that pyrophosphate is less effective than orthophosphate as a sole phosphorus source, and (2) that the phosphate combination behaves synergistically.

EXAMPLE 2

Phosphates with chain lengths varying from 1 to 21 were evaluated by the above procedure. The results are presented as FIG. 1 and Table 2. Table 3, which is the rate of hydrolysis of typical condensed phosphate at 100° C. using distilled water, is from FMC Corporation's, *Technical Data Bulletin* 810-B. A comparison of Table 2 and Table 3 makes it clear that the variation of the rates of cell growth is not dependent upon the rates of hydrolysis of the condensed phosphates to orthophosphate.

EXAMPLE 3

The synergistic effect of a tripolyphosphate and an orthophosphate was demonstrated using the above procedure and using varying amounts of a tripolyphosphate and sufficient orthophosphate to maintain a constant phosphorus content in the media. The results are presented as Table 4. The cell growth rate was normalized with an internal standard of orthophosphate. All values are averages of duplicates. The theoretical cell growth was calculated based on the relationship.

$$\frac{(\% \cdot \text{tripoly}) \times (.83) + (\% \text{ ortho}) \times 1.0}{100}$$

From Table 4 it is clear that a synergistic effect occurs when the tripolyphosphate ranges between 5% and 45% of the combined tripolyphosphate and orthophosphate in the nutrient, and is particularly evident in the range between 25% and 45%.

EXAMPLE 4

Both pyrophosphate ions and tripolyphosphate ions have the ability to sequester or complex many metal cations while orthophosphate ions have the ability to precipitate many of the metal cations that are particularly desirable as nutrients and micronutrients. The nutrient compositions of the present invention are shown to be superior to compositions of the prior art which contain only orthophosphates as a nitrogen source and selected micronutrients.

Nutrient solutions were prepared containing 100 g/l ammonium chloride and 100 g/l of an orthophosphate or a short-chain condensed phosphate as shown in Table 5 (a N:P ratio of 0.8). To these solutions the following micronutrients were successively added: 4 ml of a 1% solution of $MgSO_4.H_2O$, 2 ml of a 0.1% solution of $MnSO_4.H_2O$, 0.1% solution of $CaCl_2$, and 6 ml of a 0.65% of $FeSO_4.7H_2O$. The results are presented as Table 5.

From Example 4 it can be seen that both the pyrophosphate ion and the tripolyphosphate alone or in combination are superior to the prior art compositions in preventing precipitation of micronutrients.

EXAMPLE 5

A site 70×100 meters is contaminated with a mixture of industrial solvents composed of benzene, toluene, and xylene (BTX). The contaminate is located in both a 0.3 m saturated zone and a 0.6 m unsaturated zone. Average soil contamination is about 5,000 ppm and the groundwater shows a total BTX level of 80 ppm. The formation is a course sand and gravel able to sustain flows of 400 min, and the depth to water is 7 meters.

The site is prepared by digging an injection gallery consisting of a trench 50 m × 1 m × 1.2 m. The injection gallery is located at the spill site perpendicular to and up gradient from the natural groundwater flow to a recovery well. A 10 cm perforated pipe is placed in the bottom of the gallery on top of a 0.3 meter layer of coarse rock and covered with additional coarse rock. Down gradient, at the periphery of the soild contamination, a recovery well is installed, screened to a depth of 3 meters below the water table. The recovery well is plumbed so that the groundwater can be returned to the injection gallery.

Groundwater and core samples taken from the contaminated area are analyzed for compatibility with the treatment fluids, and an identification of indigenous hydrocarbon-degrading microorganisms of the genera pseudomonas Arthobacter, Norcardia, and Acinetobacter. The hydrocarbon-utilizing bacteria were found to be a mixed culture with a population level of $10^2$–$10^3$ colonies/gram of soil. Growth studies are conducted with groundwater samples from the site with 0.2% solution of a nutrient containing ammonium chloride, orthophosphate, and sodium tripoloyphosphate. The weight ratio of total nitrogen to total phosphorus in the microbial nutrient is 2:1 and the microbial nutrient contains 35% of the total phosphorus as tripolyphosphate and the balance as orthophosphate. Trace metals such as iron, magnesium, manganese, and calcium are added to samples. Through this study it is determined that optimum growth can be obtained by adding 0.5 mg/l iron in addition to the microbial nutrient.

The site is prepared by adding successive 1200 litre batches of 20% solution of the microbial nutrient blend until the ammonium and total phosphorus concentration, as phosphate, in the recycled groundwater reaches 200–500 mg/l. Pumping/injection rates are balanced at 200 min. Once a 200–500 mg/l concentration range is achieved circulation is continued for 2 weeks with continued addition of the microbial nutrient to maintain the required level of ammonium and total phosphate ions. Analysis of the groundwater shows that the level of hydrocarbon utilizing bacteria has increased to $10^4$ to $10^5$ colonies per ml.

After this period, a hydrogen peroxide solution, such as Restore TM 105 microbial nutrient (an aqueous solution of hydrogen peroxide manufactured by FMC Corporation) is added to the groundwater upstream of the injection gallery. The initial level of addition is 10–100 mg/l hydrogen peroxide and is continued until the bacterial count reaches $10^5$ to $10^6$ colonies/ml in the recycled groundwater. The hydrogen peroxide is increased in stages of 100 to 200 mg/l week until a level of 500 mg/l or greater is attained. The upper limit of hydrogen peroxide concentration is defined by the point at which bacterial counts decrease significantly and is generally less than 10,000 ppm or 0.1%. The injection of the microbial nutrient, iron solution, and Restore TM 105 microbial nutrient (hydrogen peroxide) is continued to maintain optimum growth.

The addition of nutrients and hydrogen peroxide is continued until analysis of the site shows that 90% to 95% of the soil contamination has been degraded by the bacteria. At this point the concentrations of ammonium and total phosphate ions are reduced to 50–100 mg/l and the hydrogen peroxide concentration is continued at 500 mg/l or higher to allow for the bacterial consumption of absorbed nutrients. When the soil contamination level is reduced to under 98% of the original, nutrient injection is discontinued and the hydrogen peroxide concentration is reduced to 100 mg/l. Injection of groundwater and peroxide is continued for an additional month. Finally, the hydrogen peroxide introduction is stopped but groundwater injection is continued until residual ammonium and phosphate concentrations meet regulatory requirements.

TABLE 1

EFFECT OF PERCENT PYROPHOSPHATE ON CELL GROWTH (AT A CONSTANT TOTAL PHOSPHORUS CONCENTRATION)

| % Pyrophosphate Added | Normalized Cell Growth |
|---|---|
| 0 | 1.00 |
| 1 | 1.29 |
| 5 | 1.36 |
| 10 | 1.43 |
| 25 | 1.22 |
| 43 | 1.12 |
| 50 | 1.17 |
| 75 | 1.08 |
| 90 | .91 |
| 99 | .82 |
| 100 | .49 |

TABLE 2

EFFECT OF CHAIN LENGTH ON CELL GROWTH

| Phosphate | Chain Length | Relative Cell Growth |
|---|---|---|
| Ortho | 1 | 1.0 |
| Pyro | 2 | .50 ± .04 |
| Tripoly | 3 | .83 ± .21 |
| Sodaphos ® | 6 | .40 |
| Hexaphos ® | 13 | .23 |
| Glass H ® | 21 | .04 |

TABLE 3

HYDROLYSIS OF POLYPHOSPHATES 1% SOLUTION IN DISTILLED WATER AT pH 8, 100° C., TIME 1.5 HOURS

| Phosphate | Chain Length | % Ortho Formed |
|---|---|---|
| Pyro | 2 | 9 |
| Tripoly | 3 | 13.5 |
| Sodaphos ® | 6 | 30 |
| Hexaphos ® | 13 | 22 |
| Glass H ® | 21 | 15 |

(Sodaphos ®, Hexaphos ® and Glass H ® are registered trademarks of FMC Corporation for sodium polyphosphates with chain lengths of 6, 13 and 21 respectively).)

TABLE 4

EFFECT ON CELL GROWTH OF COMBINED ORTHOPHOSPHATE AND TRIPOLYPHOSPHATE

| % of Phosphorous as Tripolyphosphate | Measured Cell Growth | Theoretical Cell Growth | Ratio Measured/Calculated |
|---|---|---|---|
| 0 | 1.00 | 1.00 | 1.00 |
| 1 | 1.04 | 1.00 | 1.04 |
| 5 | 1.14 | 0.99 | 1.15 |
| 25 | 1.25 | 0.96 | 1.31 |
| 43 | 1.23 | 0.93 | 1.33 |
| 66 | 0.99 | 0.89 | 1.16 |
| 100 | 0.83 | 0.83 | 1.0 |

TABLE 5

EFFECT OF PHOSPHATE TYPE ON METAL SOLUBILITY

| Phosphate Concentration (g/L) | | | | Solids Precipitated (g) | Comments |
| --- | --- | --- | --- | --- | --- |
| MSP | DSP | STPP | TSPP | | |
| 40 | 60 | 0 | 0 | 1.87 | MnSO$_4$ gave precipitate |
| 0 | 0 | 0 | 100 | 1.61 | CaCl$_2$ gave flaky precipitate |
| 40 | 0 | 0 | 60 | 1.44 | CaCl$_2$ gave heavy precipitate |
| 40 | 0 | 65 | 0 | 0 | Mn and MgSO$_4$ gave precipitate which dissolved CaCl$_2$ gave heavy precipitate which dissolved |
| 0 | 0 | 115 | 0 | 0 | Same as above |
| 40 | 0 | 32.5 | 30 | 0.13 | Mn, Mg, Ca gave precipitate which cleared Fe gave slight precipitate |

MSP = monosodium phosphate
DSP = disodium phosphate
STPP = sodium tripolyphosphate
TSPP = tetrasodium pyrophosphate

What is claimed is:

1. A process for stimulating the growth of aerobic bacteria which comprises providing aerobic conditions for the aerobic bacteria and supplying a nitrogenphosphorus nutrient supplement composition to the aerobic bacteria, said composition comprising nitrogen and phosphorus in said composition in the range of from 0.8 to 8 parts by weight of nitrogen per part by weight of phosphorus wherein the phosphorus is incorporated in the composition as an orthophosphate compound and a short-chain condensed phosphate compound and wherein from 5% to 65% by weight of the phosphorus in the combined orthophosphate compound and the condensed phosphate compound in the composition is present as the condensed phosphate compound.

2. The process of claim 1 wherein the condensed phosphate is a pyrophosphate.

3. The process of claim 1 wherein the condensed phosphate is a tripolyphosphate.

4. The process of claim 3 wherein from 25% to 45% by weight of the combined orthophosphate and tripolyphosphate is present as the tripolyphosphate.

5. A process for stimulating bacterial growth within a subterranean formation to bioxidize a contaminant in the subterranean formation which comprises supplying a nitrogen-phosphorus nutrient supplement composition to the aerobic bacteria in the subterranean formation, said composition comprising nitrogen and phosphorus in said composition in the range of 0.8 to 8 parts by weight of nitrogen per part by weight of phosphorus, wherein the phosphorus is incorporated in the composition as an orthophosphate compound and a short-chain condensed phosphate compound and wherein from 5% to 65% by weight of the phosphorus in the combined orthophosphate compound and the condensed phosphate compound in the composition is present as the condensed phosphate compound.

6. The process of claim 5 wherein the condensed phosphate is a pyrophosphate.

7. The process of claim 5 wherein the condensed phosphate is a tripolyphosphate.

8. The process of claim 7 wherein from 25% to 45% by weight of the combined orthophosphate and the tripolyphosphate is present as the tripolyphosphate.

9. The process of claim 1 wherein from 0.1 mg/l to 1000 mg/l of hydrogen peroxide is incorporated into the nutrient composition.

10. The process of claim 2 wherein from 0.1 mg/l to 1000 mg/l of hydrogen peroxide is incorporated into the nutrient composition.

11. The process of claim 3 wherein from 0.1 mg/l to 1000 mg/l of hdyrogen peroxide is incorporated into the nutrient composition.

12. The process of claim 4 wherein from 0.1 mg/l to 1000 mg/l of hydrogen peroxide is incorporated into the nutrient composition.

13. The process of claim 5 wherein from 0.1 mg/l to 1000 mg/l of hydrogen peroxide is incorporated into the nutrient composition.

14. The process of claim 6 wherein from 0.1 mg/l to 1000 mg/l of hydrogen peroxide is incorporated into the nutrient composition.

15. The process of claim 7 wherein from 0.1 mg/l to 1000 mg/l of hydrogen peroxide is incorporated into the nutrient composition.

16. The process of claim 8 wherein from 0.1 mg/l to 1000 mg/l of hydrogen peroxide is incorporated into the nutrient composition.

* * * * *